US00PP26407P3

(12) United States Plant Patent
Higaki

(10) Patent No.: US PP26,407 P3
(45) Date of Patent: Feb. 9, 2016

(54) *HYDRANGEA* PLANT NAMED 'BCHY-11.033'

(50) Latin Name: *Hydrangea macrophylla*
Varietal Denomination: BCHY-11.033

(71) Applicant: Harrison M. Higaki, San Mateo, CA (US)

(72) Inventor: Harrison M. Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 60 days.

(21) Appl. No.: 14/120,595

(22) Filed: Jun. 6, 2014

(65) Prior Publication Data

US 2015/0359153 P1 Dec. 10, 2015

(51) Int. Cl.
*A01H 5/02* (2006.01)

(52) U.S. Cl.
USPC ..... Plt./250

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — James R. Cypher; Charles R. Cypher

(57) ABSTRACT

A new and distinct cultivar of *Hydrangea macrophylla* (Thunb.) named 'BCHY-11.033' originated as a controlled cross between varieties. The variety 'BCHY-11.033' has attractive inflorescences with relatively large sepalous florets, attractive, nonuniform sepal pigmentation and good commercial characteristics. Many non-sepalous florets in the center of the inforescence make the new variety look similar to a lace-cap variety.

4 Drawing Sheets

Botanical classification: *Hydrangea macrophylla* (Thunb.) 'BCHY-11.033'.

Variety denomination: 'BCHY-11.033'.

BACKGROUND OF THE INVENTION

This invention relates to a new and distinct cultivar of the Saxifragaceae family. The botanical name of the plant is *Hydrangea macrophylla* (Thunb.) 'BCHY-11.033'.

The new cultivar originated as a seedling from a controlled cross between the unpatented variety known as '8.1' which was the seed parent and the variety 'BC8.3' which was the pollen parent. The pollen parent, 'BC8.3', is the subject of U.S. Plant Pat. No. 25,507, filed Apr. 8, 2013. 'BC8.1' has attractive inflorescences but a growth habit that is not suitable for commercial production of ornamental potted plants. 'BC8.3' has compact, attractive inflorescences with relatively large sepalous florets that surround and almost hide all of the non-sepalous florets in the center of the panicle, attractive sepal pigmentation, and stems that branch easily and are relatively strong.

The variety 'BCHY-11.033' has relatively large sepalous florets, non-uniform sepal pigmentation at maturity and good commercial characteristics. 'BCHY-11.033' has compact, attractive inflorescences with relatively large sepalous florets that surround and almost hide all of the non-sepalous florets in the center of the panicle. The color of the sepals changes as the plant ages. Below is a table comparing the new variety to similar varieties.

TABLE 1

| | New Variety 'BCHY-11.033' | U.S. Plant Pat. No. 23,757 'BC6.1' | U.S. Plant Pat. No. 25,507 'BC8.3' | Commerical variety 'Venedig' which may be U.S. Plant Pat. No. 10,928 'Venice Raven' |
|---|---|---|---|---|
| Leaf size | 9.5 cm wide × 12.5 cm long | 12 cm wide × 15 cm long | 10 cm × 16 cm | 11 cm wide × 15.5 cm long-source U.S. Plant Pat. No. 10,928 |
| Plant height | 13" in 6" pot. | 15" in 6" pot. | 15" in 6" pot | 12" in 6" pot-observed controls grown alongside 'BC6.1'. |
| Stem strength | Strong | Stems are strong but benefit from being staked | Stems are relatively strong. | Strong - observed controls grown alongside 'BC6.1'. |
| Sepal Pigmentation | Both sides of sepals are R.H.S. 68 C (red-purple group). | Upper side of sepals is R.H.S. 86 A (violet group); Under side of sepals is R.H.S. 88 D (violet group) | Upper side of sepals is R.H.S. 73A (red-purple group) in center, and margins of sepals are R.H.S. 56 A (red group). | Upper side of sepals is R.H.S. 84 A (violet group). Under side of sepals is R.H.S. 85 A (violet group) observed controls grown alongside 'BC6.1'. |
| Sepalous Floret | 70 mm | 70 mm | 50 mm to 60 mm | 70 mm-observed |

TABLE 1-continued

| | New Variety 'BCHY-11.033' | U.S. Plant Pat. No. 23,757 'BC6.1' | U.S. Plant Pat. No. 25,507 'BC8.3' | Commerical variety 'Venedig' which may be U.S. Plant Pat. No. 10,928 'Venice Raven' |
|---|---|---|---|---|
| Size-Diameter | | | | controls grown alongside 'BC6.1'. |

The new cultivar 'BCHY-11.033' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were used from the initially selected plant. Examination of asexually reproduced, successive generations grown in Half Moon Bay, Calif. show that the combination of characteristics as herein disclosed for 'BCHY-11.033' remains firmly fixed.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
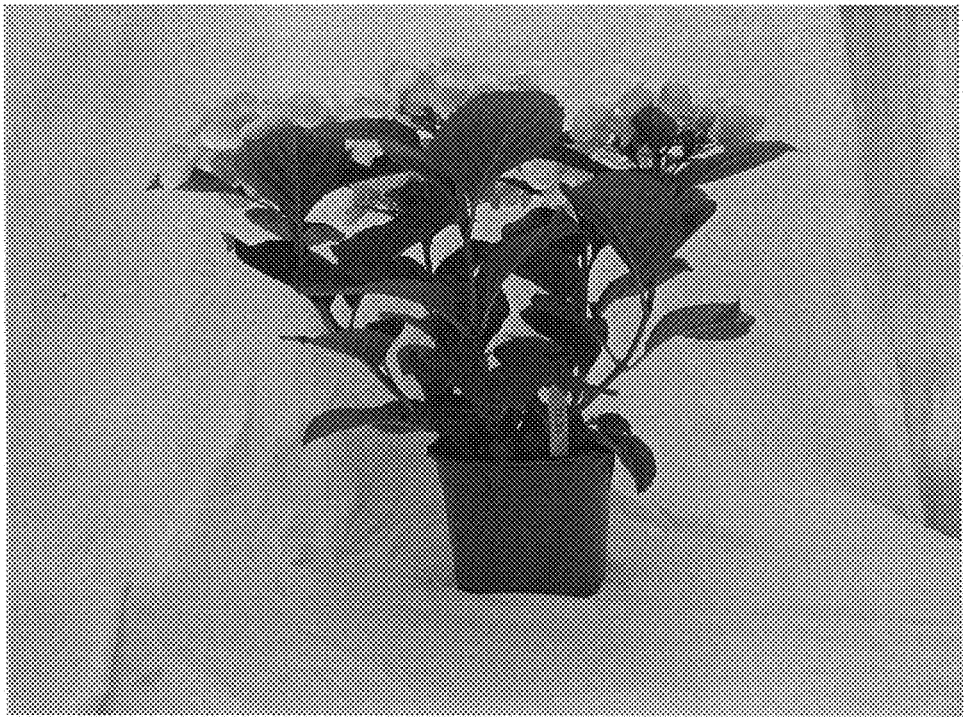
FIG. 1 is a view of the entire plant showing its form, growth habit, dark green foliage, inflorescence, and the color of its sepals.
Figure 2:
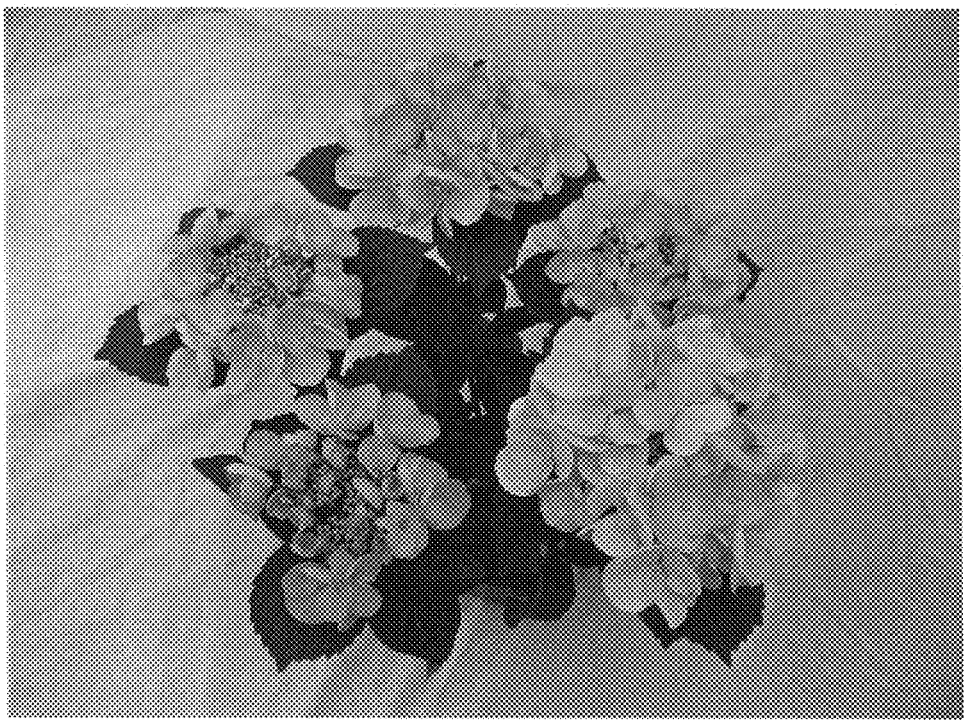
FIG. 2 is a top view of the entire plant showing its form, growth habit, dark green foliage, inflorescence, and the floor of its sepals.
Figure 3:
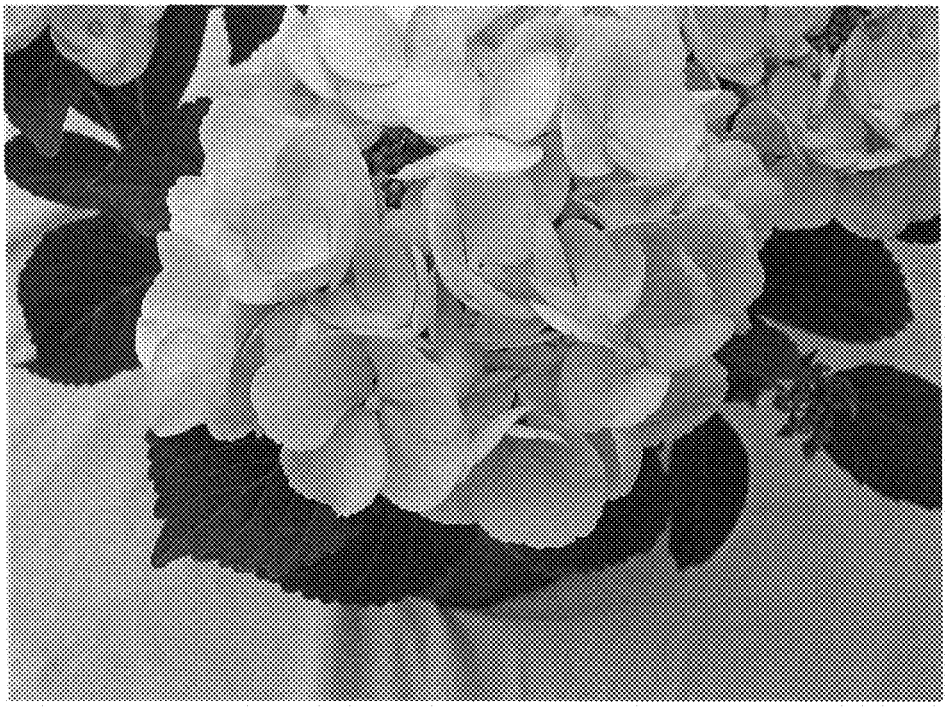
FIG. 3 is a top view of an inflorescence.
Figure 4:
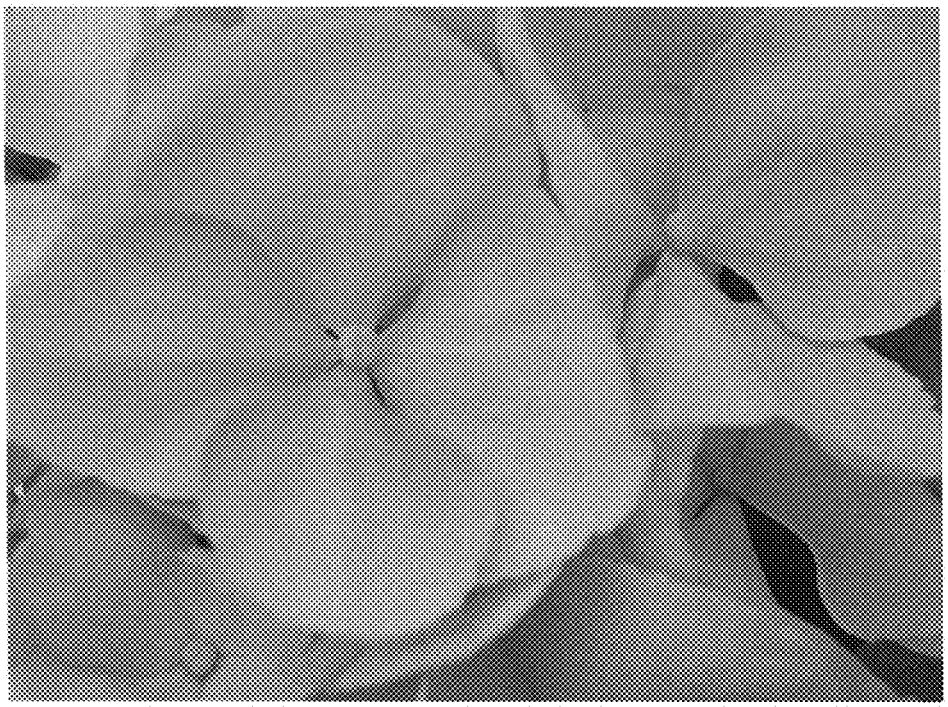
FIG. 4 is a close-up view of a floret.
Figure 5:
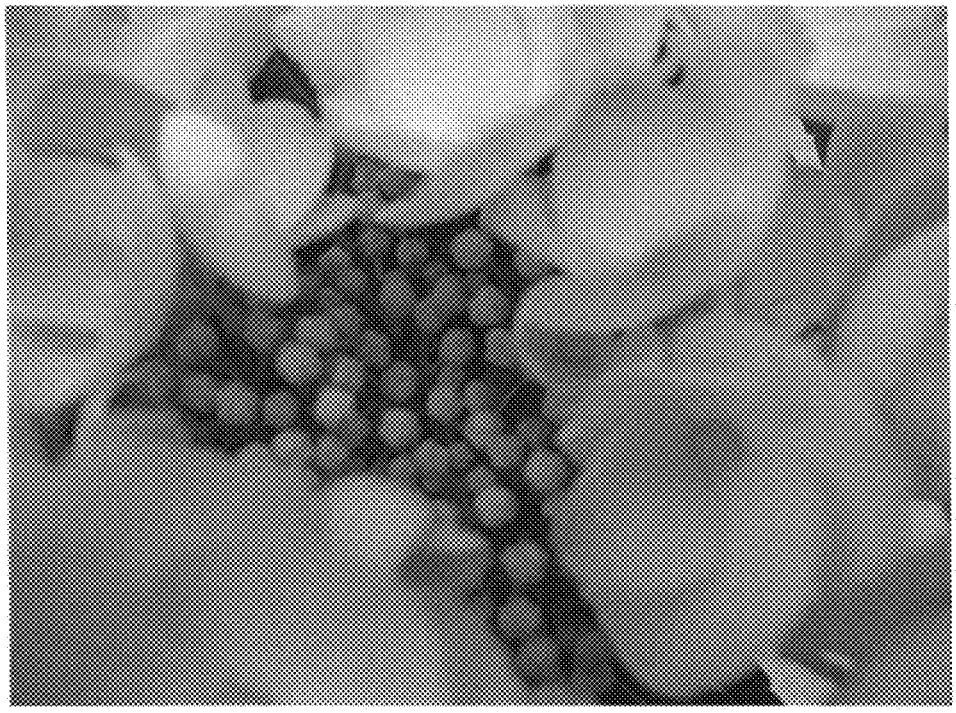
FIG. 5 is a close-up view of the upperside of a panicle of the new variety.
Figure 6:
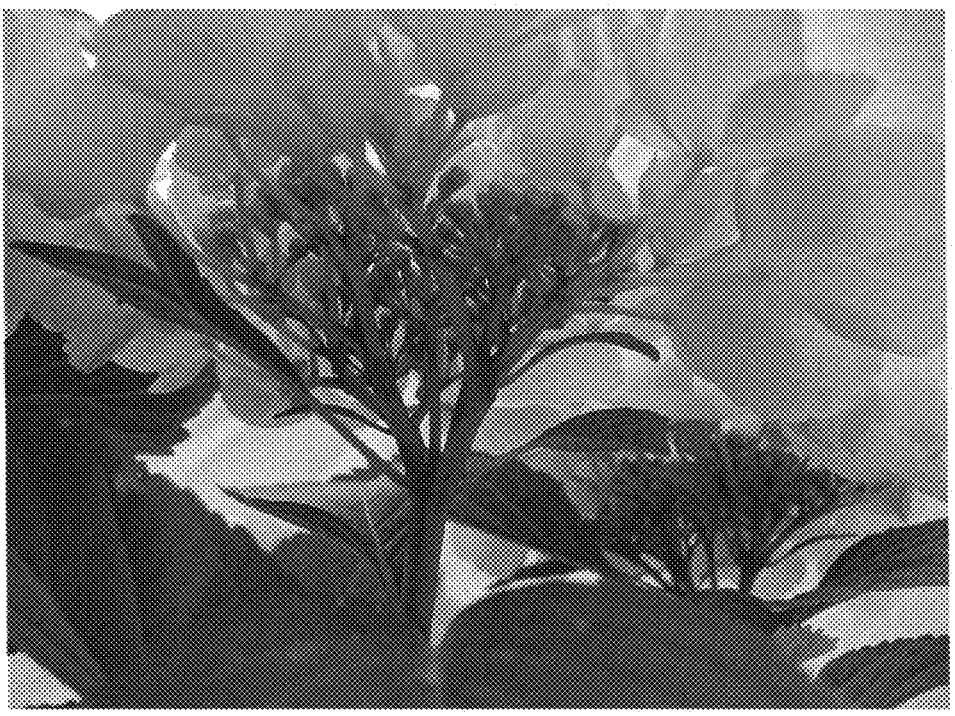
FIG. 6 is a close-up view of the underside of the panicle of the new variety.
Figure 7:
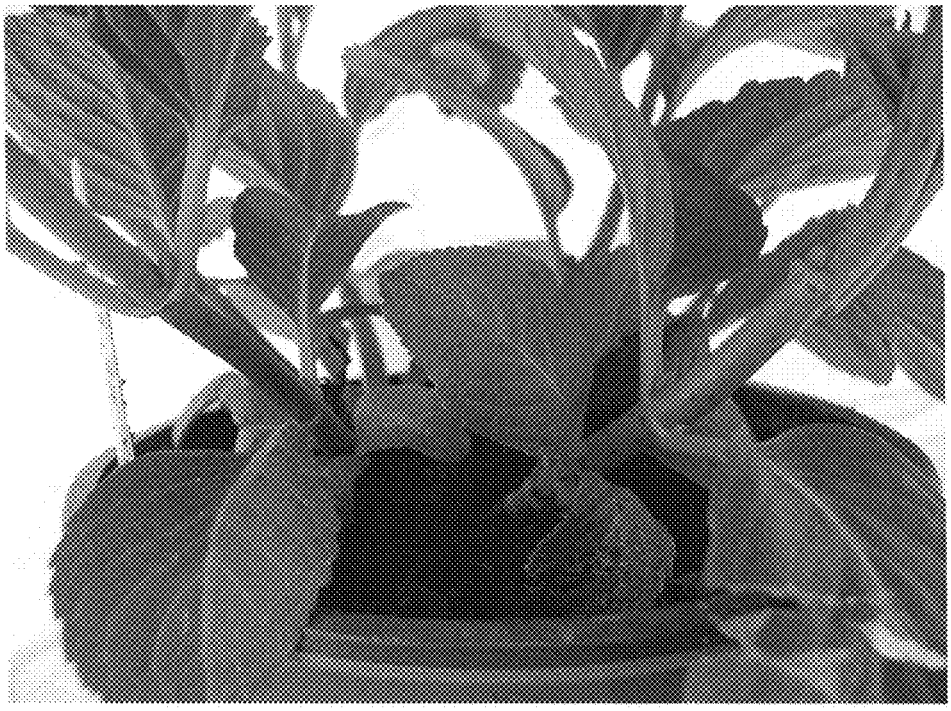
FIG. 7 is a close-up view of the base of the stem.
Figure 8:
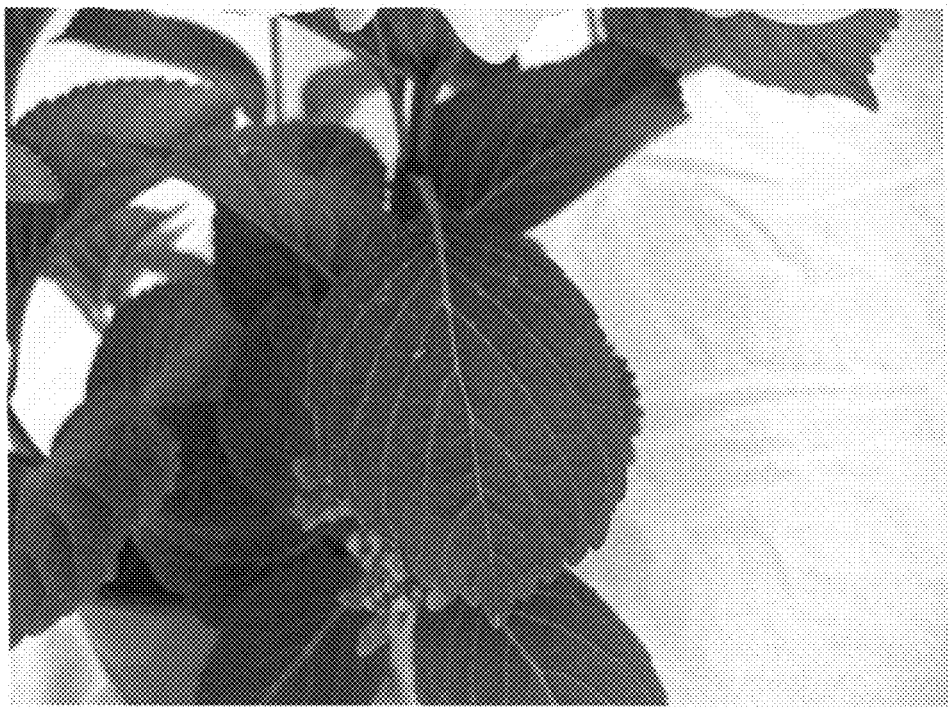
FIG. 8 is a close-up view of the adaxial surface of a mature leaf.

The plant shown is approximately a year old. The plant started out as cuttings, taken from the stem of a grown plant. The plant was pinched early to promote lateral branches.

'BCHY-11.033' has not been observed under all possible environmental conditions. The phenotype may vary significantly with variations in environment such as temperature, light intensity, treatment with aluminum and day length. Color determinations were made with The Royal Horticultural Society (R.H.S.) Colour Chart, developed in association with the Flower Council of Holland, located in Lieden.

THE PLANT

Origin: Controlled cross. The new cultivar originated as a seedling from a controlled cross between the unpatented variety known as '8.1' which was the seed parent and the commercial variety 'BC8.3' which was the pollen parent. 'BC8.3' is the subject of U.S. Plant Pat. No. 25,507, filed Apr. 8, 2013.

Form: Upright, compact shrub. A typical plant with a mature inflorescence that is ready for sale is approximately 13" high and has a diameter of 18" when grown in a 6" pot with appropriate soil amendments.

Growth: Upright, vigorous growth habit. Inflorescence is large. The plant branches easily with shoots forming at the base of the plant. Lateral branches are similar in appearance and form to the main stems.

Stems: Lenticels are present. Lenticels are R.H.S. 86 A (violet group) and are 1 to 3 mm long. The surface of young stems is glabrous. Stems become woody as they age. The color of typical young stems and young lateral branches is R.H.S. 146 C (yellow-green group). The older portions of the stems are R.H.S. 199 A (grey-brown group). Younger portions of the stems are 7 mm in diameter. Older portions of the stems are 7 mm in diameter.

Foliage: Abundant. Leaves are opposite on stem and lateral branches.

*Shape of leaf*.—Ovate with rounded base and acute apex. Margins are serrate.

*Texture*.—Glabrous; veins dominate on the underside of the leaf and are sunken on the upper leaf surface.

*Color*.—Mature leaves have an upper side that is R.H.S. 147 A (yellow-green group), and an under side that is R.H.S. 138 A (green group). Leaves are pinnately veined. The midvein and veins branching off the midvein are large and prominent on the underside of the leaves. Veins are R.H.S. 145 A (yellow-green group). Leaves are as wide as 9.5 cm and 12.5 cm long. Petioles are smooth and approximately 2.5 cm long and 4 mm wide. Petioles are R.H.S. 145 A (yellow-green group).

BUDS

Form: Globose with 4 to 5 connate, elliptic, smooth petals. Most buds, whether they will mature into sepalous or non-sepalous florets, have 5 petals. Buds in the center of the inflorescence are non-sepalous. The minority of buds will develop into sepalous florets. They are approximately 2 mm by 2 mm when very young. Buds can be 5 mm in diameter and still unopened. Color of mature buds is R.H.S. 73 B (red-purple group).

Aspect: Smooth.

Arrangement: Borne on branched panicles.

INFLORESCENCE

Form: Paniculate. Terminal. As many as 150 individual florets (both sepalous and non-sepalous) per inflorescence. Both sepalous florets and non-sepalous florets borne on the same panicle. Flowers do not produce a fragrance. The peduncle for the inflorescence is strong and upright. Many non-sepalous florets developing early on cymes that are later almost all hidden by sepalous florets that form at the outside of the panicle. Florets, both sepalous and non-sepalous, have anthers and style. Inflorescences are long-lasting, up to six weeks.

Size of inflorescence: Compact and flat. Individual inflorescence size is dependent on the number of florets. A typical inflorescence can grow as large as 9" in diameter, and 4" high.

Shape: Clusters of numerous small florets; sepalous florets overlap one another. Sepals are persistent.

Appearance: Showy.

FLORETS

General: The non-sepalous florets at the center of the inflorescence open first. Sepalous and non-sepalous florets are perfect and complete. Corolla: Generally, for both sepalous and non-sepalous florets there are 5 petals. Petals are typically 4 mm long and 3 mm wide. Petals are R.H.S. 73 B (red-purple group). Lenticels are present on pedicels of both sepalous and non-sepalous florets, lenticels are no more than 1 mm to 4mm long and very narrow. Lenticels are R.H.S. 59 B (red-purple group). Pedicel length for non-sepalous florets averages 4 mm. Pedicel length of sepalous florets is approximately 30 mm in length for plants of this age. Pedicels of both sepalous and non-sepalous florets continue to elongate as the inflorescence ages. Pedicels range from 68 C (red-purple group) to R.H.S. 146 C (yellow-green group) near floret when mature.

Stamens: 8 to 10 stamens. Anther is regular and basally attached.

Stigma: Two to three style each, although most florets have two style. Each style has one stigma.

Ovary: Ovary is partially inferior.

Sepalous florets:

*General*.—Veins dominate on the underside of the sepals.

*Number of sepals*.—4 to 5 sepals per floret, usually 4.

*Aspect of sepals*.—Smooth and glaucescent.

*Shape of sepals*.—Reniform with acuminate apex. Edges are entire, but with much crenation.

*Size of sepals*.—As the florets mature, the sepals enlarge and overlap each other more and more, until, often, there is no space between the sepals when the petals of the florets open. Sepals at maturity are typically 35 mm long and 40 mm wide. Sepalous florets are typically 70 mm in diameter. The upper sides of the sepals are R.H.S. 68 C (red-purple group) and the undersides are the same. Pigmentation develops at the tips of the sepals and travels inward towards base of the sepals. Pigmentation lightens as the sepals reach maturity. Pigmentation of mature florets is 73 D (red-purple group).

Fruit: None.

Disease and pest resistance: Unknown.

I claim:

1. A new and distinct *Hydrangea macrophylla* plant named 'BCHY-11.033' substantially as herein illustrated and described.

* * * * *